United States Patent [19]
Gysling

[11] B 3,989,732

[45] Nov. 2, 1976

[54] PHOTOSENSITIVE COPPER (I) COMPLEXES

[75] Inventor: Henry J. Gysling, Rochester, N.Y.

[73] Assignee: Eastman Kodak Company, Rochester, N.Y.

[22] Filed: Oct. 25, 1974

[21] Appl. No.: 518,656

[44] Published under the second Trial Voluntary Protest Program on February 17, 1976 as document No. B 518,656.

Related U.S. Application Data

[62] Division of Ser. No. 365,375, May 30, 1973, Pat. No. 3,860,500.

[52] U.S. Cl. ........................... 260/438.1; 96/38.4; 96/48 R; 96/88; 204/15; 204/38 R
[51] Int. Cl.² ............................................. C07F 1/08
[58] Field of Search ................................ 260/438.1

[56] References Cited
UNITED STATES PATENTS

| | | | |
|---|---|---|---|
| 2,199,944 | 5/1940 | van Peski et al. | 260/438.1 X |
| 2,909,544 | 10/1959 | Birum | 260/438.1 |
| 3,505,093 | 4/1970 | Schultz | 117/36.8 |

OTHER PUBLICATIONS

Chemical Abstracts, v 76, 46248j (1972).
Chemical Abstracts, v 75, 56372p (1971).
Chemical Abstracts, v 76, 93025u, 93030s (1972).
Chemical Abstracts, 79, 73081t (1973).

*Primary Examiner*—Helen M. S. Sneed
*Attorney, Agent, or Firm*—Arthur H. Rosenstein

[57] ABSTRACT

A novel copper (I) complex having the formula $$Cu[P(OR)_3]_n BH_3 CN$$

wherein R is lower alkyl and $n$ is an integer from 1 to 3 is employed as an actinic radiation sensitive component in an imaging process comprising imagewise exposing a support carrying the copper (I) complex to actinic radiation and developing an image in a chemical or physical development bath. The complex has excellent speed and may be handled under room light conditions prior to development.

5 Claims, No Drawings

PHOTOSENSITIVE COPPER (I) COMPLEXES

This is a division of application Ser. No. 365,375, filed May 30, 1973, now U.S. Pat. No. 3,860,500 issued Jan. 14, 1975.

This invention relates to photography and more particularly to a novel copper (I) complex and a process of forming images in an actinic radiation sensitive element comprising exposing a support carrying photosensitive copper (I) complexes to actinic light and developing the image.

U.S. Pat. No. 3,650,748, issued Mar. 21, 1972, describes physical developers comprising copper complexes and reducing agents comprising phosphine boranes.

It is known in the art to employ certain copper (I) salts with silver halide emulsion layers to be exposed to actinic light and developed to an image. U.S. Pat. No. 3,565,622, issued Feb. 23, 1971, describes the use of cuprous thiocyanate with silver halide to form a visible image after development with an amine complexing agent. Additionally some species of copper (I) complexes with ligands and anions are described in S. J. Lippard and P. S. Welcher, Inorganic Chemistry, Vol. 11, No. 1, 1972 (pages 6 to 11).

Thermographic copy sheets incorporating a copper (I) complex as the heat sensitive component are described in U.S. Pat. No. 3,505,093 issued Apr. 7, 1970. This patent describes the imagewise exposure of the complexes to heat to produce an image.

German Pat. No. 950,428, issued Oct. 11, 1956, describes the use of copper (I) salts such as cuprous chloride as photosensitive compounds. These salts are, however, insensitive to light in the dry state and must be moistened to provide light sensitivity. Further, the copper (I) salts have poor speed and are unstable in the air.

The use of cuprous oxide as a photosensitive compound has been disclosed in British Pat. No. 1,306,362. This compound, however, is not photosensitive to light in the dry state and is not colorless and leaves an undesirable background with poor image differential.

The preparation of printed circuits has generally comprised imagewise exposing a photoresist material followed by removal of exposed or unexposed areas and etching and subsequent electroplating. This method is expensive, does not allow for room light handling, the raw stock is generally unstable, the bleaching steps or etching steps pose solution disposal problems and the method requires a multitude of process steps and a great deal of equipment.

No class of copper compounds has been found in the prior art that (1) will form a well defined image after exposure to actinic radiation at high speed and development, (2) can be handled in normal room light, (3) exposed in a dry state, and (4) is stable to humidity and oxidation.

Accordingly, it is an object of this invention to provide a method of exposing an actinic radiation sensitive copper material and developing an image that is resistant to oxidation and stable in the presence of moisture.

It is another object of this invention to provide a method of exposing copper (I) complexes to actinic light to form catalytic centers for decomposition of physical developers.

Still another object of this invention is to provide copper (I) complexes that have sensitivity restricted to the UV region allowing their imagewise exposure to actinic radiation and development under ambient lighting conditions.

Yet another object of this invention is to provide a method of exposing copper (I) complexes to actinic light, heating the exposed element to enhance development and developing to form an image.

Still an additional object of this invention is to provide printed circuits by coating a support with a photosensitive copper (I) complex and exposing imagewise to actinic light and developing the exposed portions of the element by physical development of the latent image.

These objects of the present invention are accomplished by employing a light sensitive copper (I) complex represented by the formula $$Cu[P(OR)_3]_n BH_3CN$$

wherein R is a lower alkyl and $n$ is 1 to 3 as the light sensitive material in a process comprising imagewise exposing a support carrying a light sensitive material to actinic light and providing an image by either physical or chemical development.

The novel copper (I) complex is represented by the formula $$Cu[P(OR)_3]_n BH_3CN$$

wherein R is alkyl, preferably containing from about one to about four carbon atoms such as methyl, ethyl, propyl, isopropyl, and butyl, and the like; and $n$ is an integer from 1 to 3.

The preferred complexes of this invention are
 $Cu[P(OCH_3)_3]_3 BH_3CN$
 $Cu[P(OC_2H_5)_3]_3 BH_3CN$
 $Cu[P(OC_3H_7)_3]_3 BH_3CN$
 $Cu[P(OC_4H_9)_3]_2 BH_3CN$
and the like.

The novel complexes may be prepared by reacting cuprous salts such as cuprous chloride with a trialkylphosphite. The cuprous salts and the trialkylphosphite are generally mixed in an inert solvent such as chloroform, methylene chloride, ethylene chloride, and the like. The reactants may be mixed at room temperature without the aid of catalysts. To the reactants are added a salt of the cyanoborohydride such as $NaBH_3CN$ generally in solution with a solvent such as methanol, ethanol or the like. The preferred molar range of cuprous salt to phosphite is from 1.0 to 0.2. The copper (I) complex is crystallized out after the addition of the cyanoborohydride salt by cooling generally to about −15°C to about 5°C.

Alternatively, the copper (I) complex may be prepared by reducing a copper (II) salt. This method entails reducing a cupric salt such as cupric chloride in a solvent such as ethanol with excess trialkylphosphite. The molar proportion of phosphite to cupric salt is generally from about 1.5 : 1 to about 4 : 1. No special conditions are necessary for the reaction and the reactants may be mixed at room temperature if desired. The resulting product is further reacted with a salt of the cyanoborohydride such as $NaBH_3CN$. No special conditions are necessary for this reaction. The molar proportion of the cyanoborohydride salt to the above reaction products may generally be from about 1 : 1 to about 2 : 1. The copper (I) complex is then crystallized out by cooling.

The photosensitive complex may be either imbibed into a substrate or coated onto the substrate in a hydrophilic binder prior to imagewise exposure. Thus the substrate may be dipped in a bath of the complex and dried to render the element photosensitive or, if desired, and a method specifically useful in forming printed circuits, the complex may be added to a binder solution and coated onto the substrate by any means, such as dip coating brushing, rolling, spraying or the like and then dried.

The binder used as a vehicle for the photosensitive complex may be any of the hydrophilic binders used in photographic elements, including natural materials such as gelatin albumin, agar-agar, gum arabic, alginic acid, etc., and synthetic materials such as polyvinyl alcohol, polyvinyl pyrrolidone, cellulose ethers, partially hydrolyzed cellulose acetate and the like. The complex may be used with varying amounts of binder material. Preferably the complex to binder weight ratio is from about 3: 1 to about 1 : 2.

The complex may be either imbibed into or coated onto any substrate typically used for photographic elements. Support materials used herein are subject to wide variation. Glass may be employed as may be metals such as aluminum, copper, zinc, and tin. Conventional film bases, such as cellulose acetate, cellulose nitrate, cellulose acetate butyrate, poly(ethylene terephthalate), polystyrene and paper are also used. The supports generally suitable for imbibing are porous supports such as paper. Generally the supports should contain from about 1 to about 200 mg per square foot of copper (I). The preferred support materials, when the process is to be used to form an element for use as a printed circuit are poly(ethylene terephthalate), polyimides, and cellulose acetate.

The coated support is dried and may then be stored for convenient periods of time prior to imagewise exposure as the complexes are not sensitive to ambient light, nor to the humidity in the atmosphere.

The elements are typically exposed through a pattern of light, providing a latent image corresponding to the exposed or unexposed areas. The complexes are sensitive to actinic light such as ultraviolet rays generally in the wavelength range of 1800 to 4000 Angstroms. Many sources of ultraviolet light may be used such as high vapor mercury lamps, carbon arc lamps, and the like. It is noted that the copper complexes of the invention may be exposed at projection speed range (less than $10^3$ ergs/cm$^2$) which has been heretofore unattainable with copper materials.

In some instances, the rate of development of the coated supports is considerably accelerated by heating the exposed elements prior to treatment with the developer. In this respect, the required exposure time may be considerably shortened by heating the element after exposure and prior to development. Generally, the element may be heated to about 100°C to about 200°C for about 1 to about 60 seconds to exhibit this effect.

The latent image in the exposed elements can be developed into a desired metal image, typically a visible image, by either physical development or chemical development.

The physical development may take place in any conventional physical developing bath. The physical development bath generally contains metal ions in salt form and a reducing agent for the metal ions. Typical physical developer solutions are well known (see Hornsby, *Basic Photographic Chemistry*, (1956) 66, and Mees and James, ed. *The Theory of the Photographic Process*, 3rd edition (1966), 329–331, and U.S. Pat. No. 3,650,748 to Yudelson et al, issued Mar. 21, 1972) and contain the metallic ions such as silver, copper, iron, nickel, or cobalt necessary to form a visible image at and in the vicinity of the nucleating centers.

The preferred metal salts are water soluble salts such as silver nitrate, cupric salts such as copper chloride, copper nitrate, copper sulfate, copper formate, copper acetate and the like, and nickel salts such as nickel chloride, nickel bromide, nickel sulfate, nickel nitrate, nickel formate and the like.

Typical reducing agents used in the physical developer include, for example, polyhydroxy-substituted aryl compounds such as hydroquinones, catechols and pyrogallols; ascorbic acid derivatives; amino-phenols; p-phenylenediamines, and the like developing agents used in the photographic art. Particular examples of reducing agents for physical developer solutions are 2-methyl-3-chlorohydroquinone, bromohydroquinone, catechol, 5-phenyl-catechol, pyrogallol monomethyl ether (1-methoxy-2,3-dihydroxybenzene) and 5-methylpyrogallol monomethyl ether, isoascorbic acid, N-methyl-p-aminophenol, dimethyl-p-phenylene diamine, 4-amino-N,N-di(n-propyl) aniline and 6-amino-1-ethyl 1,2,3,4-tetrahydroquinoline and borane reducing agents such as amine boranes, borohydrides and the like.

The preferred physical development baths include the Copper Enthone developer baths. (A trademark of Enthonics Corp.) containing copper sulfate, formaldehyde, Rochelle salt and nickel sulfate.

The physical developer solutions can, in addition to the metal salt, reducing agent, and a complexing agent such as Rochelle salt or other ligand for the metal salt, include a variety of other materials to facilitate maintenance and operation of the developer and to improve the quality of the developed image, such as acids and bases to adjust pH, buffers, preservatives, thickening agents, brightening agents, and the like. The rate of development can be increased, and hence the time of development decreased, by adding to the developer solution a surfactant such as an alkyl metal salt of a sulfated fatty acid, e.g., dodecyl sodium sulfate.

The proportions in which the various components of the physical developer are present in the developer solution can vary over a wide range. Suitable concentrations of reducible heavy metal salt can range from about 0.01 mole to about 1.0 mole of metal salt per liter of solution. The upper limit of concentration is dependent upon the solubility of the particular metal salt employed. Preferably, the solution is about 0.1 molar to about 0.3 molar with respect to the heavy metal salt. The relative proportions of metal salt and complexing agent are dependent upon the particular heavy metal salt or salts and the particular complexing agent or agents which are employed. As a general rule, sufficient complexing agent should be incorporated to "tie up" the reducible heavy metal ions which are in solution and to lessen the tendency of these metal ions to be reduced prior to use of the developer solution. Depending upon the particular heavy metal salt and the particular complexing agent which is employed, the amount of complexing agent present typically can vary from about 0.2 mole to about 10 moles of complexing agent per mole of metal salt present. Typically, the reducing agent can be present in amounts from about 0.01 mole to about 5 moles of reducing agent per mole of metal salt present in the solution. In order to permit the developer solution to be utilized for its maximum life, at least one equivalent of reducing agent should be present in the solution for each equivalent of reducible heavy metal salt.

The physical developers are operative over a wide range of pH. However, since the borane reducing agents undergo an acid catalyzed hydrolytic reaction which reduces their stability during storage, it is preferred that the physical developers be maintained at a moderately alkaline pH of about 8 to 11, and preferably of about 8.5 to 9.5. Nevertheless, the physical developers can be used under acidic conditions, as low as pH 3, if such conditions are advantageous for the particular photographic process in which they are used. The physical developer solution can be brought to the desired pH by addition of an appropriate amount of a suitable base; for example, ammonium hydroxide or sodium hydroxide, and can be maintained at the desired pH by addition of a suitable buffering system, for example, sodium carbonate and sodium bicarbonate. Other materials which can be used to adjust the pH to the desired range and buffers which will maintain the pH in that range can be readily determined by those skilled in the art.

The exposed elements may also be developed chemically by immersing in solutions comprising aminophenols, phenyleneamines, hydroquinones, amino-dialkylanilines, heterocyclic chemical developers such as phenyl pyrazolidone and the like. A complete description of chemical developer solutions which may be used herein can be found in Mees and James, *The Theory of the Photographic Process*, 3rd ed., Chapter 13 (1966).

The process outlined above may yield a positive or negative image depending on the complex used in the physical development process.

The developed elements of the invention are especially advantageous as they have add-on capabilities. That is, the complexes remaining in the undeveloped areas are not affected by ambient light and portions of the developed element may be further imagewise exposed to actinic light and developed to produce an additional image on the element.

The process of this invention is particularly useful in forming elements for use as printed circuits. In this method, insulating supports are either imbibed with the copper (I) complexes or coated with the complexes in a binder and dried. The coated supports are imagewise exposed to actinic light so that the exposed portions are catalytic to the physical deposition of a metal such as copper, silver or nickel by physical development. The exposed element is then physically developed in a metal salt containing bath such as in a copper physical development bath and the metal such as copper is deposited and built up on the exposed portions of the element only. The element may then be dried, and if desired, a heavier build up of metal may be achieved in the exposed areas by electroplating over the element. The completed element may then be used to form a printed circuit.

The following examples are included for a further understanding of the invention.

EXAMPLE 1

To a solution of 1.7 g $CuCl_2 \cdot 2H_2O$ in 50 ml of methanol were added 6.2 ml of $P(OCH_3)_3$. After cooling the reaction solution at 0°C the product was filtered, washed with ethanol and ether and recrystallized from a 3 to 1 cyclohexane-chloroform solution. The resulting complex had the formula $$Cu[P(OCH_3)_3]Cl$$

To a solution of 5.1 g of the above complex in 125 ml chloroform was added a solution of 1.7 g of $NaBH_3CN$ in 60 ml of methanol. The reaction solution was diluted with 80 ml of chloroform, stirred for 20 minutes at room temperature and filtered through a fine sintered glass frit. The filtrate was concentrated to dryness yielding 4.9 g of a white powder having the formula $$Cu[P(OCH_3)_3] BH_3CN$$

EXAMPLE 2

A paper support was imbibed with a solution of 400 mg of the cyanoborohydride complex of Example 1 in 25 ml chloroform and dried. After a 15 second imagewise exposure to actinic light under a UVS-11 Mineralight lamp at a distance of 1.5 centimeters, negative images were obtained by immersing in the following physical developers:

1. 6 g dimethylamineborane dissolved in 50 ml water and 100 ml of a solution comprising nickel chloride, 0.224 M, citric acid 0.375 M, and ethanolamine 0.671 M. and
2. 1.5 g dimethylamineborane dissolved in 50 ml water and 100 ml of a solution comprising 29.6 g per liter of $CuCl_2 \cdot 2H_2O$ and 75 g per liter $Na_4P_2O_7$ at a pH of 10.5, $(NH_4OH)$.

The development of the above complex was compared to the photosensitivity of a similar complex having the formula $$Cu[P(OCH_3)_3]Cl$$

by imbibing 220 mg of this complex and 10 ml chloroform into a paper support and drying. The coated paper was imagewise exposed for 60 seconds to actinic light under a UVS-11 Mineralight lamp and immersed in the above two physical developers. No development was obtained.

EXAMPLE 3

The photosensitivity of $Cu[P(OCH_3)_3] BH_3CN$ was evaluated by imbibing a paper support with a solution of 400 mg of the complex and 25 ml chloroform and exposing to actinic light under a Bausch and Lomb high intensity monochrometer and physically developing by immersing in a Copper Enthone developer. The region of sensitivity was found to extend to 398 nm and the threshold exposure for imagewise development at 255 nm was 190 ergs/cm² which is well within the projection speed range.

The photosensitivity of the above complex was compared to that of three similar complexes prepared in the same manner. The complexes which were exposed and developed under the same conditions as that used for $Cu[P(OCH_3)_3] BH_3CN$ were $Cu[P(CH_3)_3]_3BH_3$ $Cu[As(C_6H_5)_3]_3BH_3CN$ and $Cu[P(C_6H_5)_3]_3BH_3CN \cdot CHCl_3$ all of which were prepared in chloroform.

The threshold exposure at 255 nm for the control complexes were 4,800 ergs/cm² for $Cu[As(C_6H_5)_3]_3BH_3CN$ and $1.1 \times 10^6$ ergs/cm² for $Cu[P(C_6H_5)_3]_3BH_3CN$. The $Cu[P(CH_3)_3]_3BH_3CN$ complex oxidized before the threshold exposure could be determined.

Thus is it seen that the novel copper (I) complex of this invention is photosensitive to actinic light in the projection speed range while the arsenic complex was much slower, the trimethyl derivative was unusable and the triphenyl derivative had a speed which was slower than 1 million ergs/cm².

EXAMPLE 4

A paper support was imbibed with a 5% solution of $Cu[P(OCH_3)_3]BH_3CN$ in chloroform and was imagewise exposed under a Gates lamp at a distance of 12 inches for 15 seconds. The exposed element was then chemically developed in a solution containing 120 g KOH and 130 g paraformaldehyde in 1 liter of water. The developer was maintained at 60°C and immediate development to a negative copper image was obtained.

EXAMPLE 5

A solution comprising 10 ml of a 20% by weight solution of poly(ethylacrylate-acrylic acid) in chloroform, 10 ml of the cyanoborohydride copper (I) complex of Example 1 in chloroform (10% by weight), and 4 drops of 1,4-butanediol diglycidyl ether is coated onto a poly(ethyleneterephthalate) support. The coating is cured by heating at 40°C overnight.

A printed circuit is prepared by imagewise exposing the dried element to a low pressure mercury arc through a stainless steel mask for 30 to 60 seconds. The exposed element is then physically developed in a Copper Enthone developer for 10 to 20 minutes at 32°C.

Although the invention has been described in considerable detail with reference to certain preferred embodiments thereof, it will be understood that variations and modifications can be effected without departing from the spirit and scope of the invention as described hereinabove.

We claim:

1. A copper (I) complex having the formula $$Cu[P(OR)_3]_nBH_3CN$$

wherein R is alkyl containing one to four carbon atoms and $n$ is an integer from 1 to 3.

2. The complex of claim 1 having the formula $$Cu[P(OCH_3)_3]BH_3CN$$

3. The complex of claim 1 having the formula $$Cu[P(OC_2H_5)_3]_3BH_3CN$$

4. The complex of claim 1 having the formula $$Cu[P(OC_3H_7)_3]_3BH_3CN$$

5. The complex of claim 1 having the formula $$Cu[P(OC_4H_9)_3]_2BH_3CN$$

* * * * *